(12) United States Patent
Laufer et al.

(10) Patent No.: US 7,066,944 B2
(45) Date of Patent: Jun. 27, 2006

(54) SURGICAL FASTENING SYSTEM

(76) Inventors: Michael D. Laufer, 1259 El Camino Real, Suite 211, Menlo Park, CA (US) 94025; Sanjay S. Bagade, 4870 Country La., San Jose, CA (US) 95129

( * ) Notice: Subject to any disclaimer, the term of this patent is extended or adjusted under 35 U.S.C. 154(b) by 90 days.

(21) Appl. No.: 10/798,018

(22) Filed: Mar. 11, 2004

(65) Prior Publication Data

US 2005/0203552 A1    Sep. 15, 2005

(51) Int. Cl.
*A61B 17/08* (2006.01)
(52) U.S. Cl. ........................... 606/151; 606/142
(58) Field of Classification Search ........ 606/1, 606/60, 63, 64, 72, 76, 77, 78, 151–158, 606/213–221; 128/887
See application file for complete search history.

(56) References Cited

U.S. PATENT DOCUMENTS

| | | | |
|---|---|---|---|
| 4,006,747 A | 2/1977 | Kronenthal et al. | |
| 4,669,473 A * | 6/1987 | Richards et al. | 606/215 |
| 4,705,040 A | 11/1987 | Mueller et al. | |
| 5,203,864 A | 4/1993 | Phillips | |
| 5,320,633 A | 6/1994 | Allen et al. | |
| 5,376,097 A | 12/1994 | Phillips | |
| 5,680,981 A | 10/1997 | Mililli et al. | |
| 5,941,439 A | 8/1999 | Kammerer et al. | |
| 5,980,524 A * | 11/1999 | Justin et al. | 606/75 |
| 6,022,373 A | 2/2000 | Lehmann | |
| 6,039,753 A | 3/2000 | Meislin | |
| 6,113,611 A | 9/2000 | Allen et al. | |
| 6,287,323 B1 * | 9/2001 | Hammerslag | 606/214 |
| 2001/0010005 A1 * | 7/2001 | Kammerer et al. | 606/151 |
| 2003/0097148 A1 | 5/2003 | Valimaa et al. | |
| 2003/0187465 A1 | 10/2003 | Bailly et al. | |
| 2004/0044364 A1 * | 3/2004 | DeVries et al. | 606/213 |

* cited by examiner

*Primary Examiner*—Glenn K. Dawson
(74) *Attorney, Agent, or Firm*—Levine Bagade LLP

(57) ABSTRACT

Devices and systems related to surgical fasteners and more specifically to surgical fasteners suitable for use in both open procedures, and minimally or less invasive procedures where the operative site is remote from the surgeon.

28 Claims, 9 Drawing Sheets

SURGICAL FASTENING SYSTEM

FIELD OF THE INVENTION

The present invention relates to surgical fasteners and more specifically to surgical fasteners suitable for use in both open procedures, and minimally or less invasive procedures where the operative or surgical site is not directly accessible by the surgeon.

BACKGROUND OF THE INVENTION

Surgical fasteners are known to be an alternative to traditional suturing techniques for procedures involving tissue closure, connection, or repair. One undesirable aspect of manual suturing is that the suturing process adds time to the overall surgical process. Moreover, manual suturing often requires that the operative area is readily accessible so that the medical practitioner can manipulate the suture and associated needle through both sides of the tissue, connection or repair site. Presently, surgical fasteners are known to provide a means to close an open surgical incision or wound, hold together pieces of soft tissue, attach devices to tissue, or repair torn tissue in orthopedic/musculoskeletal applications. Such surgical fasteners are often used where there is adequate access to the operative area, or for invasive, open procedures.

Due to the inherent risks and complexities of invasive surgical procedures, there is an increasing need for the ability to perform surgical procedures in a minimally invasive manner. In most cases, the recuperative time and lowered expense of a minimally invasive procedure makes it a far more desirable option to an alternative comparable invasive/open surgical procedure. The use of surgical fasteners in minimally invasive procedures may be desirable to increase the speed and efficiency of the procedure. Such fasteners may also open the possibility of performing a minimally invasive procedure for what was previously limited to an open surgical procedure.

In addition, suturing techniques requires considerable skill and dexterity especially when tying knots in the suture or otherwise manipulating the suture. The ability of a medical practitioner to manipulate a suture as well as knot the ends of the suture are further complicated when the site is not directly accessible to the practitioner. In such cases, even if the complexity of suturing does not prevent the procedure from being completed in a minimally invasive manner, the length of the procedure is likely to increase.

Conventional fasteners do not easily lend themselves for use in minimally invasive surgical procedure. As one example, the complexity of the known fastener-delivery devices requires devices with large profiles and limited flexibility further thereby limiting the potential for such devices to access remote locations. Conventional surgical fasteners, especially, "I-shaped" or "H-shaped" fasteners are unsuitable for remote procedures due to their complex deployment mechanisms and inability to navigate tortuous pathways using access devices commonly used for minimally invasive procedures (e.g., catheters, introducer devices, scope-type devices such as endoscopes, bronchoscopes, colonoscopies, etc.). Examples of such fasteners and devices are discussed in U.S. Pat. No. 4,006,747 to Kronenthal et al., U.S. Pat. No. 4,235,238 to Ogiu et al., U.S. Pat. No. 4,669,473 to Richards et al., U.S. Pat. No. 5,941,439 to Kammerer et al,. U.S. Pat. No. 6,039,753 to Meislin, and U.S. Patent Publications US2003/0097148 to Valimaa et al, U.S. 2003/0187465 to Bailly et al. Each of the foregoing patents and/or patent applications is hereby incorporated in their entirety by reference.

SUMMARY OF THE INVENTION

The present invention includes a surgical fastener for deployment through a device (such as a needle, cannula, catheter, etc.), where the fastener comprises a first anchor member, a second anchor member, and a connecting portion separating the first and second anchor members, where at least the first anchor member and the second anchor member each are expandable from a first state to a second state where the second state is of a larger size than the first state, where the larger size may be achieved by an increase in displacement (e.g., volume, profile, configuration, etc.) of a portion of the fastener or the entire fastener. For example, as it assumes the second state, the anchor may change in shape or conform to a profile that is of a larger size than the profile of the first state. Alternatively, or in combination, the increase in volume may be achieved by relaxing a previous state of compression of the fastener portion. In the latter case, the fastener portion may comprise a resilient material that is compressible, and/or the fastener portion may be hollow, or have a cavity, such that the outer perimeter of the anchor portion may be folded into the cavity to assume the first state, or compress the cavity to conform to a smaller state.

The surgical fastener may also comprise a first means for anchoring the fastener, a second means for anchoring the fastener and a connecting portion separating the first and second means for anchoring. Where the means for anchoring may be any of the anchor portions described herein.

The invention also includes a surgical fastening system comprising, a tubular member having a proximal and distal end and a lumen extending therebetween, the tubular member being sufficiently flexible to navigate tortuous anatomical passages within a human body, a distal portion located at the distal end of the tubular member, the distal portion having a distal tip being configured to pierce tissue, the distal portion having a lumen extending between the tubular member lumen and an opening in the distal portion, at least one surgical fastener slidably located entirely inside the tubular member lumen, where the surgical fastener comprises a first anchor member, a second anchor member, and a connecting portion separating the first and second anchor members, and an advancing member slidably located within the tubular member lumen such that advancement causes a distal portion of the advancing member to advance the surgical fastener through the tubular member. The system of the present invention may be directed to the desired site using a catheter-guidewire configuration, shaped catheter, a steerable catheter, a scope-type of device (e.g., such as endoscopes, gastroscope, colonoscope, bronchoscope, or any type of scope used to access sites within the body.)

It should be noted that alternate variations of the present invention include fastening system of the present invention used with conventional fasteners and/or fasteners of as described herein.

The present invention is useful in many surgical procedures requiring fastening systems, including but not limited to, procedures for fastening or repairing tissue or attachment of implant materials to tissue. The present invention is suitable for, but not limited to, use in the heart, stomach, gastro-intestinal tract, etc. While the faster and fastening system may be used in open procedures, the devices and systems may also be used in minimally invasive procedures where the operative site is remotely accessed using minimally invasive techniques including catheterization and/or endoscopic or similar means.

The inventive devices are especially suited for advancement via a minimally invasive technique by providing features which improve the ability of the surgeon to deploy the fastener with accuracy and effectuate a proper seal with the fastener. The minimally invasive technique also may allow for visual inspection of the placement of the anchor.

This application incorporates by reference an application filed Mar. 11, 2004 entitled "SURGICAL FASTENER" having application Ser. No. 10/798,465.

DETAILED DESCRIPTION OF THE INVENTION

The following illustrations are provided as variations of the present invention. It should be understood that there are many combinations of the present invention and that figures illustrating all variations of the invention would be numerous. Therefore, the invention is intended to include combinations of aspects and features of the illustrated embodiments, or combinations of the specific embodiments themselves.

Figure 1A:
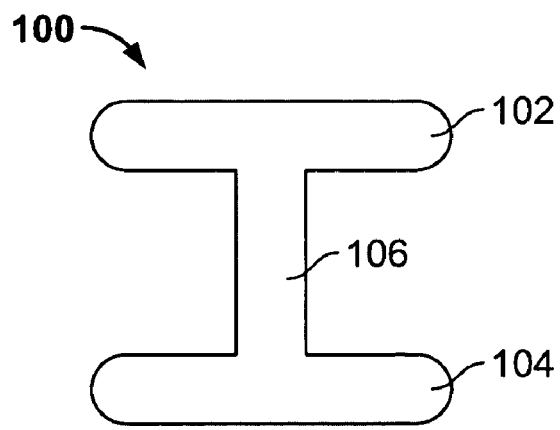
FIGS. 1A–1B, illustrate a side view of a basic variation of a fastener of the present invention.
Figure 1B:
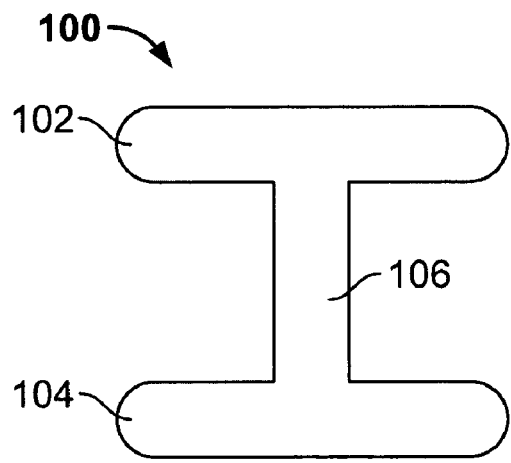

FIGS. 1A–1B, illustrate a side view of a basic variation of the inventive fastener 100. As seen in FIG. 1A, the fastener 100 includes a first anchor member 102 and a second anchor member 104 and a connecting portion 106 separating the two anchor members 102 104. The "I-type" fastener shape illustrated in FIGS. 1A–1B is merely for illustrative purposes. Naturally, the anchor portions 102 104 may have a variety of shapes, cross-sections, and configuration as discussed herein. However, the anchor portions 102 104 will generally have a shape that allows for retention of a medium (for example, torn/damaged tissue, two or more discrete pieces of tissues, one or more implants to tissue, a combination thereof, etc.) between the anchor portions 102 104 upon deployment of the anchor 100. Portion(s) of the fastener 100 will be operable between a first and second state where in the second state, a portion or portions of the fastener 100 will be of a larger size and/or profile than the first state. In the variation shown in FIG. 1B, the fastener 100 anchors 102 104 are configured so that they expand from the first state, shown in FIG. 1A, to a larger second state.

In use, the fastener 100 may be delivered to the operative site when the portions of the fastener 100 are in the first state. Upon deployment, selected portions of the fastener 100 assume the larger second state. This configuration allows for delivery of the fastener 100 through an opening in the medium where the opening is smaller than a diameter (or other similar dimension) of the fastener 100 portions after deployment. In some variations of the invention, construction of the fastener 100 allows only a portion (e.g., a single anchor, both anchors, the connecting portion, or a combination thereof) to expand into the second state. In other variations, the entire fastener 100 may be constructed to assume the second state upon deployment. It is contemplated, that the various portions of the fastener 100 may expand differently as required for the particular application (e.g., one or more portions expand at a different rate, a different size, etc.)

Expansion of the fastener 100 from the first to the second state may be accomplished a variety of ways. For example, the fastener 100 may be constructed of a shape or material that allows compression of the fastener portion, either by application of a compressive force or application of a vacuum, etc. Alternatively, or in combination, the fastener 100 may include a material that swells or expands given the addition of a fluid (e.g., natural body fluids or fluids introduced during the surgical procedure.)

Examples of these materials include biodegradeable and non-biodegradeable polymers, elastomers, shape-memory alloys, other alloys, etc.) For example, carbonate copolymer, polyether ester copolymer, albumin, gelatin, starch, cellulose, dextrans, polysaccharides, fibrinogen, poly (D,L lactide), poly (D,L-lactide-co-glycolide), poly (glycolide), poly (hydroxybutyrate), poly (alkylcarbonate) and poly (orthoesters), EVA copolymers, silicone rubber and poly (methylmethacrylate). Particularly preferred polymeric carriers include poly (ethylene-vinyl acetate), poly (D,L-lactic acid) oligomers and polymers, poly (L-lactic acid) oligomers and polymers, poly (glycolic acid), copolymers of lactic acid and glycolic acid, poly (caprolactone), poly (valerolactone), polyanhydrides, copolymers of poly (caprolactone) or poly (lactic acid) with polyethylene glycol, PET, PETE, and blends thereof.

In any case, the second state of the fastener comprises a larger profile or configuration as compared to the first state. As stated above, this permits securing of the anchoring portions 102 104 about the medium and/or securing of the connecting portion 106 within the medium. Another advantage of the invention is that the opening in the medium created during deployment of the fastener 100 may be smaller than would otherwise be possible if the fastener did not expand into the second state upon or after deployment.

It is also contemplated that the fastener may incorporate a variety of additives, coatings, adjuncts, etc. For example, the fastener (or only portions of the fastener) may include a lubricious coating to improve advancement of the fastener in the delivery system. The fastener may include non-proliferative drugs, thrombogenic additives, non-thrombogenic additives, non-inflammatory medicines, additives to induce fibrosis for wound closure, anti-platelet, anti-coagulent, growth factors, gene-transductors, cell matrix, glue, cement, protein, hydrophilic, hydrophobic, lipidphillic, lipidphobic, or combinations where appropriate.

Figure 2A:
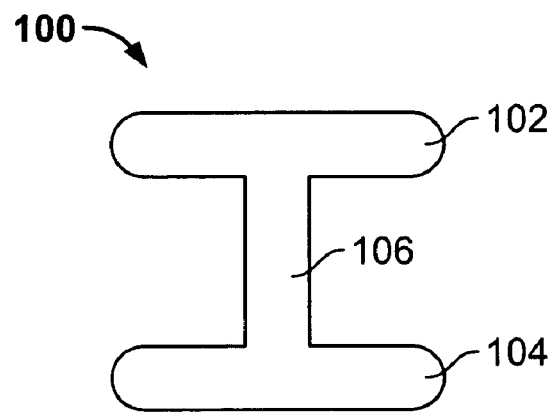
FIGS. 2A–2H illustrate additional examples of various fasteners.

FIGS. 2A–2H illustrate examples of various fasteners 100 of the present invention. It should be understood that the fasteners 100 of the present invention may have a number of configurations as required for the specific application. These figures are intended to illustrate some possible variations of the invention. As noted herein, where possible, combinations of features of various embodiments and the embodiments themselves are within the scope of the invention. FIG. 2A illustrates a fastener 100 similar to that shown in FIGS. 1A–1B. FIG. It is contemplated that for the basic configuration of the fastener 100 illustrated in FIG. 2A (and where appropriate for other variations) the anchor portion 102 104 or the connecting portion 106, individually or collectively, may have cross sections of a variety of shapes, including but not limited to circular, rectangular, square, star-shaped, etc.

Figure 2B:
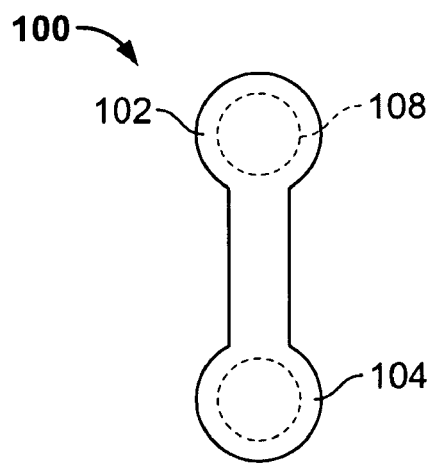

FIG. 2B illustrates a variation of the fastener 100 where the anchor portions 102 104 have a spherical shape. In this variation, the anchor portions 102 104 are illustrated as having a cavity 108. The cavity 108 may assist in reducing the size of the anchor portions 102 104 into the first state. Moreover, as described herein, the cavity 108 (as well as other portions of the fastener 100) may serve as a reservoir for various medications, drugs, etc. Furthermore, variations of fasteners of the present invention may be non-porous if the particular application requires (e.g., where prevention of tissue in-growth is required. Alternatively, variations of the fastener may be porous. Furthermore, the fastener may be selected such that certain portions of the fastener are porous while others are non-porous (e.g., porous anchor members combined with a non-porous connecting member, non-porous anchors with a porous connecting member, etc.) In such variations, porous materials may be selected for construction of the anchor or non-porous materials may be altered to contain pores.

Figure 2C:
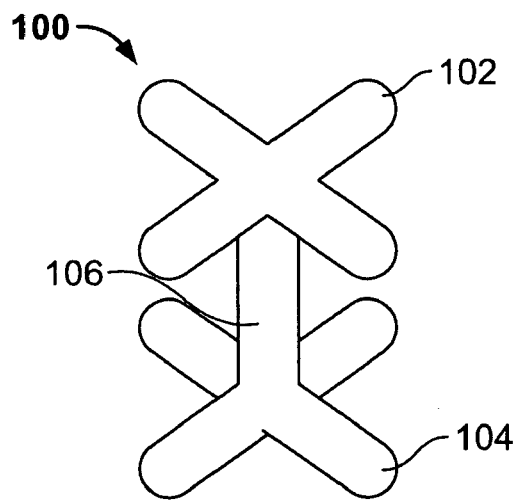
Figure 2D:
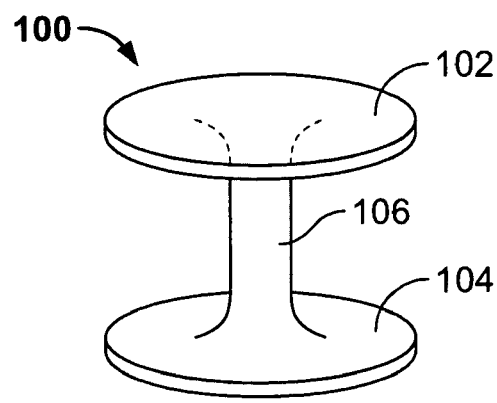
Figure 2E:
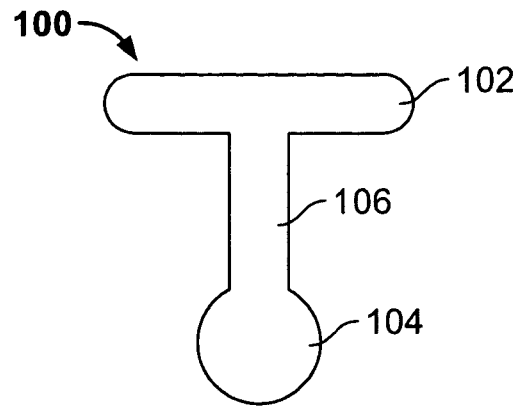

FIG. 2C illustrates another variation of the fastener 100 in which the anchor portions 102 104 comprise cross-shaped members. FIG. 2D illustrates a fastener 100 having anchor portions 102 104 that are planar-disc-shaped. In such a configuration, the increased surface area of the anchor portions 102 104 may provide better contact between the fastener 100 and the medium to allow for tissue in-growth or for delivery of a therapeutic substance carried by the fastener 100. FIG. 2E illustrates a variation of a fastener 100 of the present invention where the first anchor portion 102 and the second anchor portion 104 comprise different shapes. It should be noted that variations of the invention include fasteners 100 having combinations of anchor portions as illustrated herein or variations thereof.

Figure 2F:
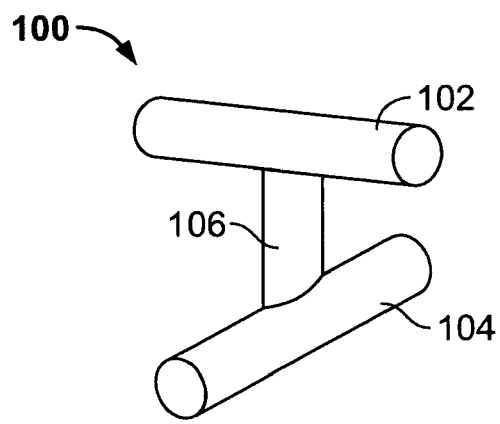

FIG. 2F illustrates a variation of a fastener 100 of the present invention where the first anchor portion 102 and the second anchor portion 104 extend in different directions.

Figure 2G:
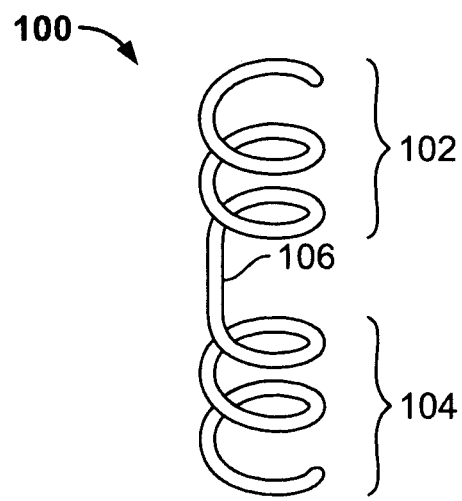

FIG. 2G illustrates a variation of the fastener 100 of the present invention where the anchor portions 102 and 104 comprise "pig-tail" type fasteners. In this variation, the anchor portions 102 and 104 the coils of the pig-tail may separate to capture tissue therebetween. Alternatively, the opposing anchor portions 102 and 104 may be used to capture the tissue. During placement of the fastener 100 the pig-tail anchors may be straightened in the device for delivery. Alternatively, the coils may be compressed in a radial dimension to expand upon deployment from the delivery system. A variation of a pig-tail fastener may include a helical shaped fastener or fastener with helical anchor portions.

Figure 2H:
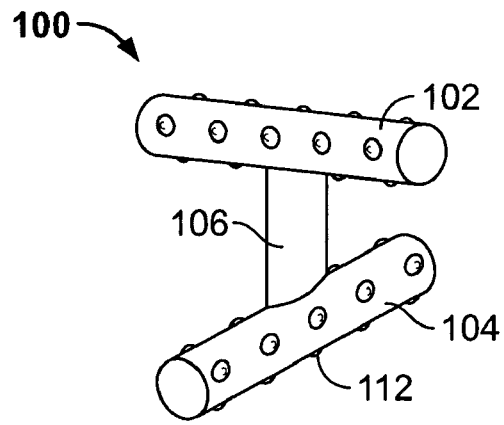

FIG. 2H illustrates another variation of the invention where a fastener 100 includes protrusions 112. The protrusions 112 may assist in retaining the anchors and or fastener in the deployment site. Alternatively, or in combination, the protrusions 112 may comprise bio-active substances as described herein. Although the figure illustrates the protrusions as on the anchor portions only, the invention includes fasteners 100 having protrusions 112 on the connecting portion 106 as well. Alternatively, the protrusions 112 may be located only on the connecting portion 106.

The invention also contemplates that the anchor portions described herein may be configured/suited for attachment of external devices/implants/objects/etc. For example, one possible use of the inventive fastener is placing the fastener in the wall of an organ, then attaching an implant to the organ's wall by attaching the implant to the anchor portions of the fastener.

Figure 3A:
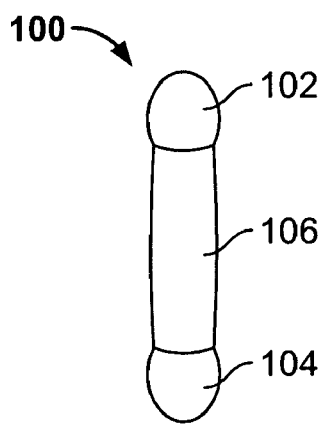
FIGS. 3A–3B illustrate a variation of a fastener having a single diameter (or similar cross-sectional measurement) prior to deployment.
Figure 3B:
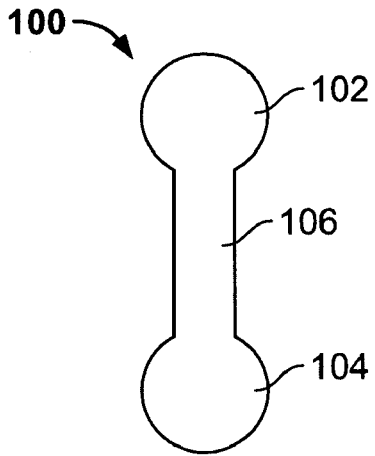

FIGS. 3A–3B illustrate another variation of a fastener 100 of the present invention. In this variation, as shown in FIG. 3A, in the pre-deployment or first state, the anchor portions 102 104 have substantially the same cross sectional measurement as the connecting portion 106. As illustrated in FIG. 3B, when the anchor portions 102 104 assume the second state, they expand to a greater size than the connecting portion 106. As discussed herein, the anchor portions 102 104 may be constructed from a material similar to that of the connecting portion 106 but having different additives or structure to allow for expansion into the second state. Alternatively, portions of the fastener 100 may be formed from different materials and joined, or molded together to form the composite fastener.

Figure 3C:
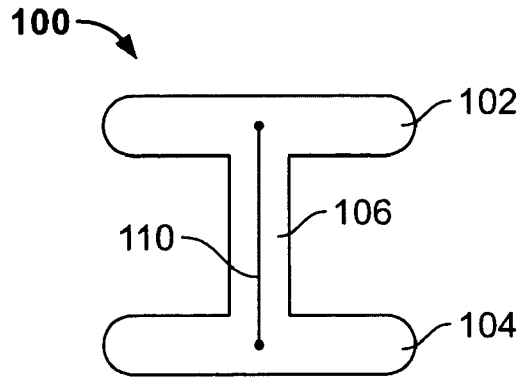
FIG. 3C illustrates a variation of a fastener having an insert.

FIG. 3C illustrates another variation of a fastener 100 of the present invention. In this variation, the fastener 100 includes an insert 110. The insert 110 may comprise a bioabsorbable material which dissolves/is absorbed by the body at a slower rate than the remainder of the fastener 100. Alternatively, the insert 110 may be a nonbiodegradeable/non-bioabsorable material such that as tissue replaces the absorbable fastener material, the insert remains to provide long term retention of tissue. Moreover, the insert 110 may comprise a metallic material to provide a radiopaque marker for placement, or for subsequent location of the fastening site. Such a combination may be used with absorbable and non-absorbable fasteners. Although the insert 110 illustrated in FIG. 3C comprises end portions having a larger dimension than the center portion, the invention is not limited as such.

Figure 4A:
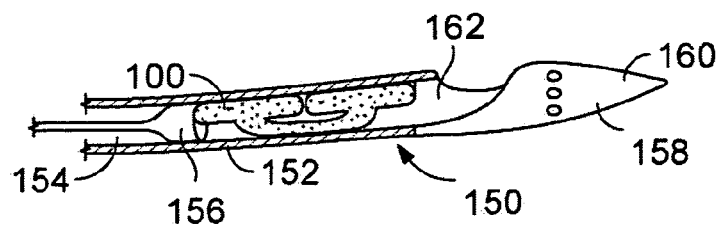
FIG. 4A–4C illustrate an example of a fastener system deploying a fastener.
Figure 4B:
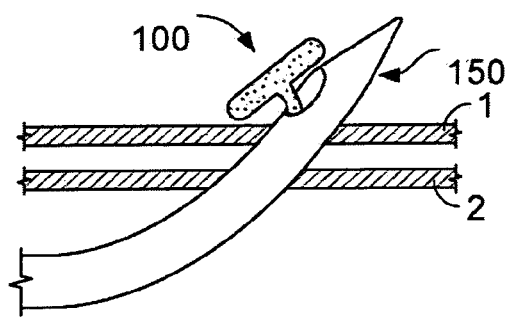
Figure 4C:
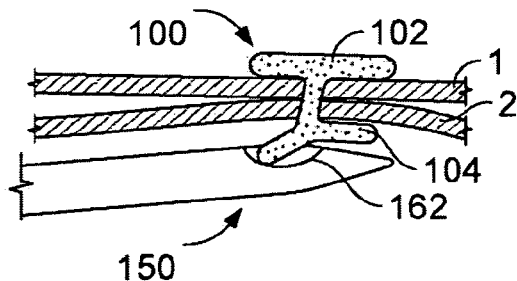

FIG. 4A–4C illustrate a basic example of a system 150 which deploys fasteners 100 of the present invention. As shown in FIG. 4A, the system 150 includes a tubular member 152 that is sufficiently flexible so that it may navigate tortuous passages to access the surgical site yet it will have sufficient column strength so that it may penetrate tissue to deploy the fastener 100. As such, variations of the tubular member 152 may be reinforced to minimize kinking of the tubular member as it navigates toward the surgical site. In this variation, the tubular member 152 retains a fastener 100 in a lumen 154 that extends between a proximal and distal end of the tubular member 152. The fastener 100 is slidably located inside the tubular member 152 and may be advanced using an advancing member 156 that is also slidably located within the tubular member lumen 154.

It is contemplated that various methods known in the field may be employed to advance/retract the advancing member. For example, the advancing member may simply push the fastener using a linear or rotary type drive system. Alternatively, the advancing member may be an auger type system that advances the fastener with the assistance of rotatable vanes within the tubular member. A pneumatic, hydraulic, or fluid filled actuation may also be used to advance/retract the advancing member. The advancing member 156 may be a guidewire or other similar type device that is able to deploy the fastener 100 at the operative site. Although not illustrated, the fastener 100 may be removably attached to the advancing member 156 to improve accuracy in deployment of the fastener 100. In some variations of the invention, the fastener 100 is configured relative to the lumen 154 so that friction retains the fastener 100 within the lumen 154 until deployment of the fastener 100. In such cases, the wall surface and/or diameter of the lumen 154 may be selected to increase the sliding resistance of the fastener 100. In any case, the system will be configured so that upon deployment of the first anchor the fastener 100 will release from the device rather than pulling out of the tissue.

The system 150 also includes a distal portion 158 located at the distal end of the system 150. The distal portion 158 has a distal tip 160 configured to pierce tissue and has an opening 162 through which the fastener 100 exits the device. In some variations of the invention, the distal tip 160 is configured to prevent "coring" of the tissue to minimize the size of any opening created during deployment of the fastener. Instead, the tip 160 configuration has a sharpened area and a taper proximal to the sharpened area so that the tip 160 makes a small puncture and then dilates the opening in the tissue.

FIG. 4B illustrates the system 150 of FIG. 4A after the distal portion 158 advances through two layers of tissue 1 and 2 and one anchor portion 102 exits from the system 150. As discussed herein, the fastener 100 may expand upon exiting the system 150 via being released from the constraint of the system 150. Alternatively, or in combination, fluids (not shown) may cause the fastener 100 to increase in size. Such fluids may be introduced during the procedure or may be naturally occurring at the operative site. Therefore, the fastener 100 may expands to a size greater than the opening in tissue that is created by the fastening system 150. Next, the distal portion 158 and tubular member 152 are retracted through the tissue 1. Once retracted, the system 150 deploys the second anchor portion (not illustrated) thereby retaining the tissues 1 between the anchor portions 102 104.

FIG. 4C illustrates the system 150 of FIGS. 4A and 4B after the distal portion 158 is withdrawn through the tissue 1 sufficiently enough so that the opening 162 is on the near side of the tissue 1. Once in the appropriate position, the device 150 deploys the remaining anchor portion 104. It should be understood that the system illustrated in FIGS. 4A–4C is depicted to show a basic variation of the invention. It is contemplated that the invention includes variations configured to first deploy an anchor portion on a near side of the tissue (e.g., prior to insertion of the distal tip into the tissue), then advance the distal tip into the tissue to deploy the remaining anchor portion on the far side of the tissue.

Figure 4D:
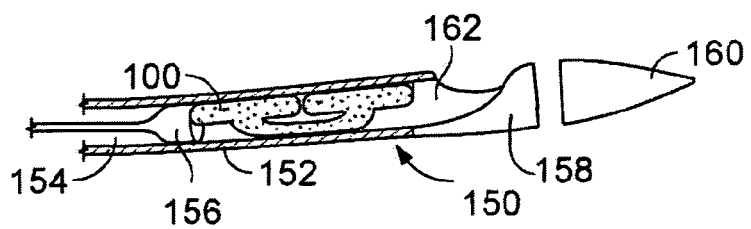
FIG. 4D illustrates a variation of a fastener system of the present invention.

FIG. 4D illustrates a variation of a fastening system of the present invention. In this variation, the distal tip 160 is inserted into the distal portion 158.

Although the fastener of the present invention may be delivered through any tubular device such as a cannula, a catheter, polymeric tubing, etc., the fastener may be part of a fastening system that permits deployment of the fastener in remote parts of the body through a variety of minimally invasive procedures. In such cases, the system may include a steerable catheter, or the system may be guided to the site via a separate catheter, a separate steerable catheter, a endoscope-type device, pre-shaped catheter, etc.

Figure 5A:
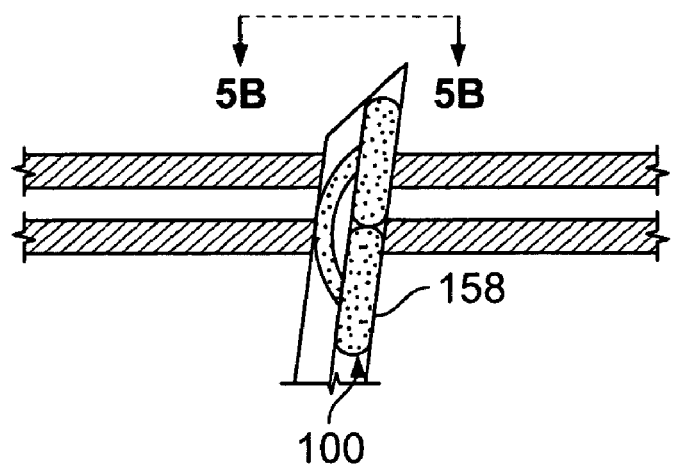
FIGS. 5A–5B illustrate another variation of a fastener system.
Figure 5B:
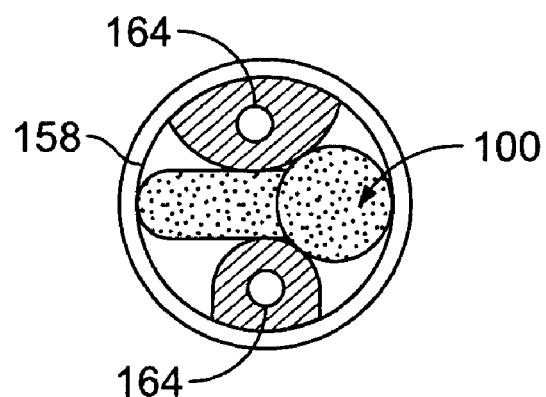

FIGS. 5A–5B illustrate another variation of a system 150 of the present invention. In this variation, the opening 162 is located at a distal end of the device rather than in a side-wall of the distal portion. In such a variation, the fastener 100 may be located immediately adjacent the opening 162 to prevent the coring of tissue as the distal tip 160 advances through tissue. FIG. 5B illustrates a sectional view taken along the line 5B–5B of FIG. 5A. As illustrated, the system 150 may include a lumen that is appropriately shaped to orient the anchor and central portions of the fastener 100. For example, the lumen may be extruded to form a channel for the central portion. Additionally, as shown in FIG. 5B, the system may include a multi-lumen design to allow for fluid delivery ports 164 if required.

As discussed herein, upon deployment of the fastener 100 from the system 150, the fastener 100 portions shall increase in size from the first state to a second state where the larger size may be achieved by an increase in volume and/or profile a portion of the fastener or the entire fastener. The invention contemplates that the fastening delivery system 150 may be used to constrain the fastener 100 into the first state, via a compression mechanism. Alternatively, or in combination, the fastener 100 or portions of the fastener may be configured to increase in size given the application of a fluid. The fluid may comprise naturally occurring bodily fluid or fluid delivered by the fastening system or even fluid delivered via a separate device.

Figure 6A:
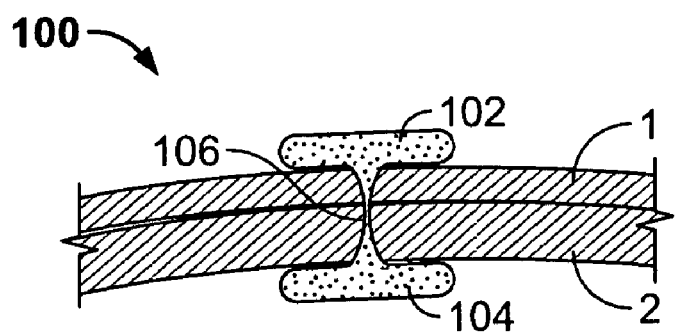
FIG. 6A illustrates a deployed fastener having elastic properties.

As discussed above, one of the functions of the inventive tissue fastener is to retain two pieces of tissue together, retain an implant to the tissue, or close an opening in tissue. The feature of the inventive fastener 100 relating to expansion of the anchor portions 102 104 permits placement of the fastener 100 using an opening in the tissue that is smaller would otherwise be required. Moreover, fasteners of the present invention may also be configured such that the central portion 106 expands into a second state as well. In such variations, expansion of the center portion may allow for expedited healing of the opening in tissue, or for closure and sealing of the opening in the tissue. In additional variations of the invention, the central portion 106 may be configured from a material that allows stretching of the center portion 106 during deployment. As shown in FIGS. 6A, such a fastener 100 having elastic properties allows for an increased compressive force on the medium being retained between the fastener. An additional benefit of such an elastic fastener is that the length of the fastener 100 (e.g., as measured in a direction along the central portion) can accommodate a greater range of tissue and/or material thicknesses.

Figure 7A:
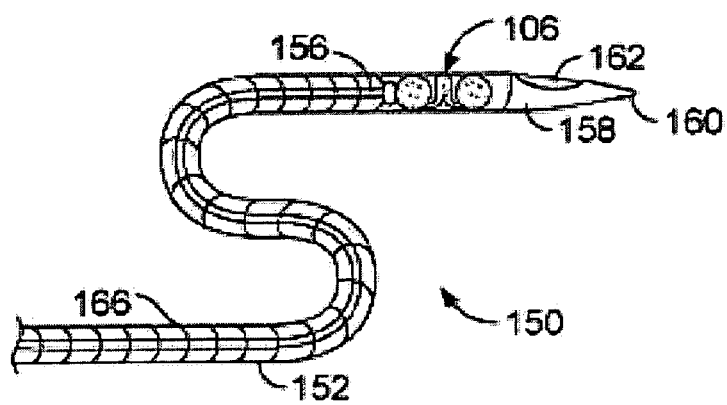
FIG. 7A–7C illustrate variations of fastening systems of the present invention.

FIG. 7A illustrates a variation of a fastening system 150 of the present invention. Although the system 150 depicts a single fastener 100 located within the device, it is contemplated that the system 150 may comprise a number of fasteners 100 to permit serial deployment during use of the system. As illustrated, the system 150 includes a flexible tubular member 152 extending between having proximal and distal ends and a lumen extending between the ends. The system 150 includes a distal portion 158 the distal end of the tubular member 152. It is contemplated that the distal portion 158 may comprise a separate material or insert that is coupled to the tubular member 152. Alternatively, the distal portion 158 may be formed from the same material as the tubular member 152. The distal portion 158 includes a distal tip 160 for penetrating tissue (and/or an implant, etc.). The distal portion 158 includes a lumen that is in fluid communication with a lumen of the tubular member 152. The distal portion 158 also includes an opening 162 through which the fastener 100 deploys.

In the illustrated variation, the opening 162 is located in a side wall of the distal portion 158. However, as discussed herein, the opening may be at the distal tip 160. It is contemplated that the tubular member 152 will have sufficient column strength to allow for penetration of tissue via advancement of the system 150. Accordingly, the tubular member 152 may be constructed of a material that provides sufficient flexibility and column strength. Alternatively, the tubular member 152 may include a reinforcing member 166, such as a coil, braid, or fiber reinforcement. Furthermore, as discussed above, the system 150 includes an advancing member 156 that permits advancement and/or deployment of the fastener r 100. To improve advancement and deployment of the fastener, the tubular member and/or advancing member may be selected from materials that minimize the friction between the two members. Alternatively, or in combination, these items may include a lubricious coating to minimize friction. Although not illustrated, the system 150 may include an additional fluid delivery means, such as a fluid source where delivery of the fluid occurs via the lumen of the device, an additional fluid lumen, a separate catheter-type device for delivery of the fluid, etc.

Figure 7D:
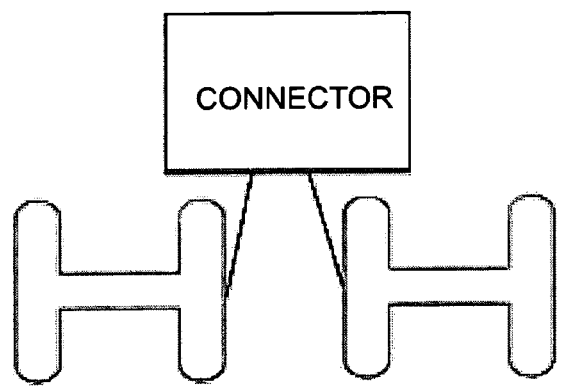
FIG. 7D illustrates a variation of the present invention where the plurality of surgical fasteners are each connected.
Figure 7B:
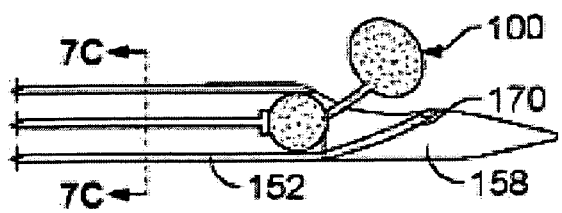
Figure 7C:
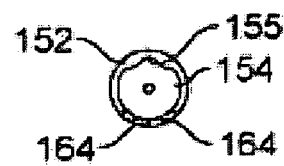

FIG. 7B illustrates an additional variation of a fastening system 150 of the present invention. In this variation, the fastener 100 is depicted as being partially ejected from the system 150. As shown, the distal portion 158 may include one or more fluid delivery ports 170 in fluid communication with fluid delivery lumen(s) 164 of the tubular member 152. FIG. 7C is a sectional view taken along the lines of 7C—7C of FIG. 7B. As shown, the tubular member 152 may include a channel 155 to aid in maintaining an orientation of the fastener and/or assist in advancement of the fastener. FIG. 7C also illustrates fluid delivery lumens 164 of the tubular member 152. It is understood that the system may include a single or multiple fluid delivery lumens(s).

FIG. 7D illustrates a variation of the present invention where the plurality of surgical fasteners are each connected.

Figure 8A:
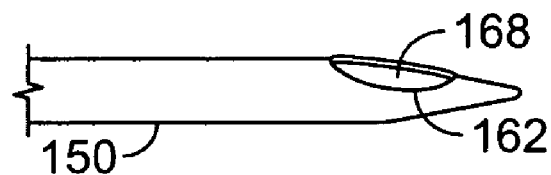
FIGS. 8A–8F illustrate additional features of fastening systems of the present invention.
Figure 8B:
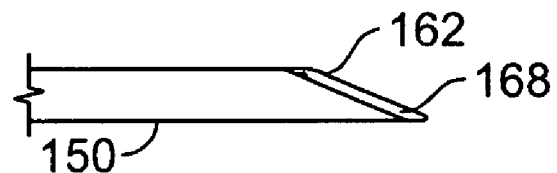
Figure 8C:
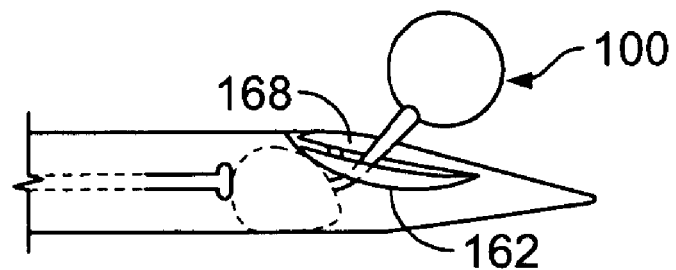

FIGS. 8A–8F illustrate variations of the fastening 150 of the present invention having features that aid in dispensing fasteners. FIGS. 8A–8C illustrate delivery systems having gate members 168 of a valve-type configuration. For example, the gate member 168 of these variations may comprise a flexible valve having a slit, gap, or opening therein. The gate member will function to impede movement of a portion of a surgical fastener from the system. Accordingly, a portion of the gate member will interfere with a portion of the fastener during its advancement in the system or out of the system. Although the gate 168 is illustrated as being placed in the opening 162 of the distal portion 158, the gate 168 may also be located within a lumen of the system. FIG. 8C illustrates a variation of the fastening system 150 of the present invention depicting a fastener 100 that is partially deployed from the system 150.

Figure 8D:
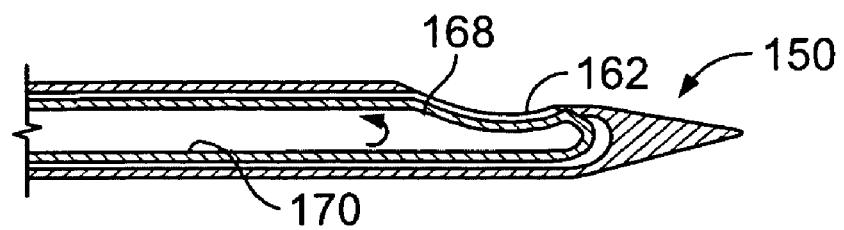
Figure 8E:
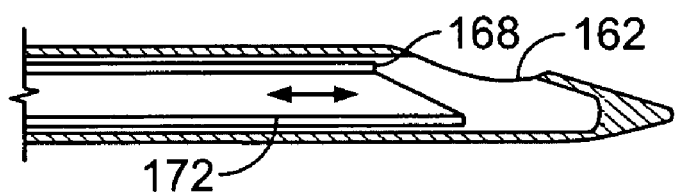

FIGS. 8D–8E illustrate additional features of a fastening system 150 of the present invention. The fastener and other features of the system are omitted for the sake of clarity. In the variation of FIG. 8D, the system 150 includes a gate member 168 located on a rotatable insert 170 located within the tubular member 152. The rotatable insert 170 may have the same or similar features of the tubular member 152 and tubular member lumen as described above. In use, rotation of the rotatable insert 170 causes the gate member 168 (which may be formed by an opening in the rotatable insert) to impinge upon a portion of the fastener (not shown) as the fastener exits from the system 150. In some variations of the invention, application of an increased torque to the gate member 170 may permit severing or cutting of the fastener or a connection between adjacent fastener. For example, some variations of the invention include fasteners that have a severable connection.

FIG. 8E illustrates a variation of the fastening system 150 where a gate member 168 is located on a distal end of a slidable insert 172. The effect of the slidable insert 172 may be similar to that of the rotatable insert described above where the operative mechanism is advancement and retraction of the slidable insert. The slidable insert 172 may move independently of any advancing member (not shown) to allow proper dispensing of a fastener.

Figure 8F:
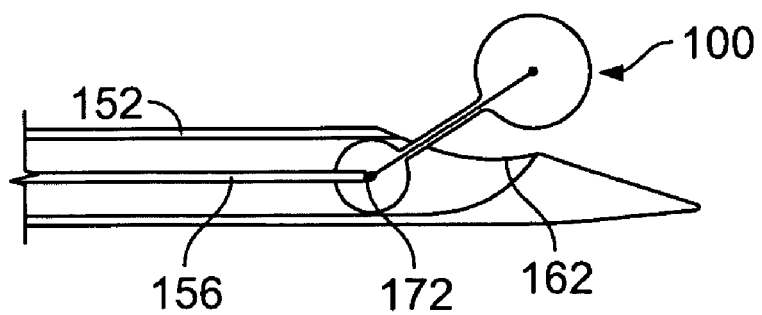

FIG. 8F illustrates another variation of a fastening system of the present invention, in this variation the fastening system 150 may include an advancing member 156 that is coupled to a fastener 100 via a detachable joint 172. The detachable joint 172 may comprise a low-melt temperature polymer that is bonded to both the fastener 100 and the advancing member 156. In such a variation, the advancing member 156 will be configured to heat the joint (for example, via conductive, resistive, chemical, etc, means.) Alternatively, the detachable joint 172 may comprise an electrolytic joint. In such a case, the fastener may comprise a metallic frame 110 as described above. In use, the fastener 100 may be positioned, and upon confirmation of its placement, the detachable joint 172 is activated to release the fastener.

We claim:

1. A surgical fastening system comprising:
   a tubular member having a proximal and distal ends and a lumen extending therebetween,
   a distal portion located at the distal end of the tubular member, the distal portion having a distal tin being configured to pierce tissue, the distal portion having a lumen extending between the tubular member lumen and an opening in the distal portion;
   at least one surgical fastener slidably located inside the tubular member lumen, where the surgical fastener comprises a first anchor member, a second anchor member, and a connecting portion separating the first and second anchor members;
   an advancing member slidably located within the tubular member lumen such that advancement causes a distal portion of the advancing member to advance the surgical fastener through the tubular member, and
   a gate member in fluid communication with the tubular member lumen or distal portion lumen, the gate member having a portion that impedes movement of at least one surgical fastener.

2. The surgical fastening system of claim 1, where the tubular member is sufficiently flexible to navigate tortuous anatomical passages within a human body.

3. The surgical fastening system of claim 1, where the surgical fastener is located entirely within the tubular member lumen.

4. The surgical fastening system of claim 1, where the gate member comprises a flexible valve, where the valve increases resistance to the fastener during advancement of the fastener.

5. The surgical fastening system of claim 1, where the gate member is moveably located in the distal portion lumen such that it may at least partially occlude the opening.

6. The surgical fastening system of claim 1, where the connecting portion of the surgical fastener has a greater elasticity than either the first or second anchor member such that when tissue is placed between the anchor members, the connecting member is placed in a tensile state providing a compressive force against the tissue by the anchor members.

7. The surgical fastening system of claim 1, where the advancing member is releasably coupled to at least one surgical fasteners.

8. The surgical fastening system of claim 1, where the opening is at the distal tip.

9. The surgical fastening system of claim 1, where the opening is in a wall of the distal portion.

10. The surgical fastening system of claim 9, where the distal tip is inserted into the distal portion.

11. The surgical fastening system of claim 1, where the surgical fastener is an I shaped, H shaped, helical shaped or pig-tail shaped fastener.

12. The surgical fastening system of claim 11, where the fastener is resilient and assumes the I shape, H shape, helical, or pig-tail shape upon deployment from the tubular member.

13. The surgical fastening system of claim 1, where the at least one surgical fastener comprises a plurality of surgical fasteners.

14. The surgical fastening system of claim 13, where the plurality of surgical fasteners are each connected.

15. The surgical fastening system of claim 1, where the tubular member comprises a reinforcing member to increase an axial strength of the tubular member.

16. The surgical fastening system of claim 1, where at least the first anchor member and the second anchor member each are expandable from a first state to a second state where the second state is of a larger displacement than the first state.

17. The surgical fastening system of claim 16, where the second state is of a larger volume than the first state.

18. The surgical fastening system of claim 16, where the first anchor member and second anchor member are compressible upon application of a compressive force and assume the second state upon removal of the compressive force.

19. The surgical fastening system of claim 18, where the first anchor member and second anchor members are sized relative to the tubular member lumen so that the tubular member provides the compressive force upon insertion of the anchor members into the tubular member.

20. The surgical fastening system of claim 18, where connecting portion is also expandable from the first state to the second state where the second state is of a larger volume than the first state.

21. The surgical fastening system of claim 16, where at least the first and second anchor members comprise a material that expands upon contact with a fluid.

22. The surgical fastening system of claim 1, where the tubular member further comprises a fluid delivery lumen, and where the distal tip further comprises a port in fluid communication with the fluid delivery lumen.

23. The surgical fastening system of claim 1, where the connecting portion has a greater elasticity than either the first or second anchor member such that when tissue is placed between the anchor members, the connecting member is placed in a tensile state providing a compressive force against the tissue by the anchor members.

24. The surgical fastening system of claim 1, where the connecting portion has a cross sectional area less than a cross sectional area of either the first or second anchor member.

25. The surgical fastening system of claim 1, where the advancing member is detachably coupled to the fastener.

26. The surgical fastening system of claim 25, where the advancing member is detachably coupled to the fastener via a detachable joint.

27. The surgical fastening system of claim 26, where the detachable joint comprises an electrolytic joint.

28. The surgical fastening system of claim 26, where the detachable joint comprises a polymer.

* * * * *

UNITED STATES PATENT AND TRADEMARK OFFICE
CERTIFICATE OF CORRECTION

PATENT NO. : 7,066,944 B2  
APPLICATION NO. : 10/798018  
DATED : June 27, 2006  
INVENTOR(S) : Michael D. Laufer et al.

It is certified that error appears in the above-identified patent and that said Letters Patent is hereby corrected as shown below:

Col. 10, claim 1, line 29, please replace:  
"tin" with --tip--

Signed and Sealed this

Twelfth Day of June, 2007

JON W. DUDAS  
*Director of the United States Patent and Trademark Office*